United States Patent
Allendorf et al.

(10) Patent No.: US 9,329,154 B1
(45) Date of Patent: May 3, 2016

(54) DEVICES AND METHODS TO DETECT AND QUANTIFY TRACE GASES

(71) Applicant: Sandia Corporation, Albuquerque, NM (US)

(72) Inventors: Mark D. Allendorf, Pleasanton, CA (US); Alex Robinson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 760 days.

(21) Appl. No.: 13/633,772

(22) Filed: Oct. 2, 2012

Related U.S. Application Data (60) Provisional application No. 61/544,078, filed on Oct. 6, 2011.

(51) Int. Cl.
  *G01N 29/02* (2006.01)
  *G01N 29/22* (2006.01)

(52) U.S. Cl.
  CPC .............. *G01N 29/22* (2013.01); *G01N 29/022* (2013.01)

(58) Field of Classification Search
  CPC .............. G01N 29/022; G01N 29/245; G01N 29/2462; G01N 29/30; G01N 29/34; G01N 29/326; G01N 29/348; G01N 29/2437; G01N 29/323
  USPC .......... 73/596–600, 645, 24.03, 24.04, 24.06, 73/24.01, 29.01, 29.02, 29.05, 73/31.01–31.05
  See application file for complete search history.

(56) References Cited

U.S. PATENT DOCUMENTS

| | | | | |
|---|---|---|---|---|
| 4,947,677 | A * | 8/1990 | Frye et al. | 73/38 |
| 5,189,914 | A * | 3/1993 | White et al. | 73/599 |
| 5,212,988 | A * | 5/1993 | White et al. | 73/599 |
| 5,235,235 | A * | 8/1993 | Martin et al. | 310/313 D |
| 5,447,845 | A * | 9/1995 | Chu et al. | 435/6.11 |
| 5,571,944 | A * | 11/1996 | Pfeifer et al. | 73/24.04 |
| 6,257,048 | B1 * | 7/2001 | Hietala et al. | 73/24.01 |
| 6,767,510 | B1 * | 7/2004 | Buechler | B01L 3/50273 422/412 |
| 7,482,732 | B2 * | 1/2009 | Kalantar-Zadeh | 310/323.21 |
| 8,065,904 | B1 * | 11/2011 | Allendorf et al. | 73/31.06 |
| 8,440,012 | B2 * | 5/2013 | Hatcher, Jr. | C23C 16/403 106/286.5 |

(Continued)

OTHER PUBLICATIONS

Sensors and Acuators B Chemical, SciVerse Science Direct, vol. B168, Jun. 20, 2012, ISSN 0925-4005.

(Continued)

*Primary Examiner* — Helen Kwok
(74) *Attorney, Agent, or Firm* — Medley, Behrens & Lewis, LLC (57) ABSTRACT

Sensing devices based on a surface acoustic wave ("SAW") device coated with an absorbent crystalline or amorphous layer for detecting at least one chemical analyte in a gaseous carrier. Methods for detecting the presence of a chemical analyte in a gaseous carrier using such devices are also disclosed. The sensing devices and methods for their use may be configured for sensing chemical analytes selected from the group consisting of water vapor, carbon dioxide, methanol, ethanol, carbon monoxide, nitric oxide, nitrous oxide, organic amines, organic compounds containing $NO_2$ groups, halogenated hydrocarbons, acetone, hexane, toluene, isopropanol, alcohols, alkanes, alkenes, benzene, functionalized aromatics, ammonia ($NH_3$), phosgene ($COCl_2$), sulfur mustard, nerve agents, sulfur dioxide, tetrahydrofuran (THF) and methyltertbutyl ether (MTBE) and combinations thereof.

20 Claims, 6 Drawing Sheets

(56) References Cited

U.S. PATENT DOCUMENTS

| | | | | |
|---|---|---|---|---|
| 8,480,955 | B2* | 7/2013 | Yaghi et al. | 422/68.1 |
| 8,674,128 | B2* | 3/2014 | Yaghi | B01J 31/1691 |
| | | | | 556/136 |
| 8,904,850 | B1* | 12/2014 | Allendorf | G01N 29/022 |
| | | | | 310/313 B |
| 2003/0082587 | A1* | 5/2003 | Seul | B01J 19/0046 |
| | | | | 435/6.12 |
| 2004/0244466 | A1* | 12/2004 | Shen | 73/24.01 |
| 2006/0032290 | A1* | 2/2006 | Liu | 73/29.02 |
| 2007/0202038 | A1* | 8/2007 | Yaghi | B01J 20/226 |
| | | | | 423/702 |
| 2008/0093226 | A1* | 4/2008 | Briman | G01N 27/127 |
| | | | | 205/775 |
| 2010/0058834 | A1* | 3/2010 | Cobianu et al. | 73/24.01 |
| 2010/0058857 | A1* | 3/2010 | Zhang | 73/335.02 |
| 2010/0132549 | A1* | 6/2010 | Yaghi | B01D 53/02 |
| | | | | 95/128 |
| 2010/0288014 | A1* | 11/2010 | Yao et al. | 73/24.06 |
| 2010/0320437 | A1* | 12/2010 | Gordon | B82Y 10/00 |
| | | | | 257/9 |
| 2011/0137025 | A1* | 6/2011 | Yaghi | B01J 20/226 |
| | | | | 540/145 |
| 2011/0197657 | A1* | 8/2011 | Gole | G01N 27/127 |
| | | | | 73/31.05 |
| 2012/0028846 | A1* | 2/2012 | Yaghi | B01J 20/226 |
| | | | | 506/39 |
| 2012/0047994 | A1* | 3/2012 | Shen et al. | 73/24.06 |

OTHER PUBLICATIONS

Metal-Organic Framework Thin Films: From Fundamentals to Applications. Angélique Bétard and Roland A. Fischer, Anorganische Chemie II, Organometallics and Materials, Ruhr-Universitat Bochum, D-44780 Bochum, Germany.

Acoustic Wave Microsensor Arrays for Vapor Sensing, Jay W. Grate, Environmental Molecular Sciences Laboratory, Pacific Northwest National Laboratory, P.O. Box 999, Richland, Washington, 99352, American Chemical Society, published on Web Mar. 28, 2000.

Ultrasensitive Humidity Detection Using Metal-Organic Framework-Coated Microsensors, Alex L. Robinson, Vitalie Stavila, Todd R. Zeitler, Michael I. White, Steven M. Thornberg, Jeffery A Greathouse, and Mark D. Allendorf, Sandia National Laboratories, P.O. Box 5800, Albuquerque, New Mexico, 87185, Sandia National Laboratories, P.O. Box 969, Livermore, California 94551.

* cited by examiner

DEVICES AND METHODS TO DETECT AND QUANTIFY TRACE GASES

CROSS-REFERENCE TO RELATED APPLICATIONS

This application claims the benefit U.S. Provisional Application No. 61/544,078 filed on 6 Oct. 2011 and entitled "MATERIALS, METHODS AND DEVICES TO DETECT AND QUANTIFY VOLATILE ORGANIC COMPOUND CONCENTRATIONS IN AN ATMOSPHERE," the entirety of which is incorporated herein by reference.

STATEMENT OF GOVERNMENT INTEREST

The United States Government has rights in this invention pursuant to Contract No. DE-AC04-94AL85000 between the United States Department of Energy and Sandia Corporation for the operation of the Sandia National Laboratories.

BACKGROUND

Porous coordination polymers ("PCP") are a class of hybrid inorganic-organic, typically crystalline materials (amorphous PCPs are also known) whose structure and properties can be rationally tailored by the selection of their component chemical moieties. Distinguishing features of a PCP are coordinating metallic groups causing organic ligands to self-organize into two- or three-dimensional open-pore structures. These structures retain their porosity upon removal of "guest" molecules (e.g., a solvent or other similar molecule), enabling them to serve as reversible sorbents for a variety of molecular species. Two broad subcategories of PCPs reported in the literature include, but are not limited to, metal-organic frameworks (MOFs) and zeolitic imidazolate frameworks (ZIFs). Covalent organic frameworks (COFs) are a related class of porous materials, in which the nanoporous structure comprises a network of main-group atoms (typically silicon and/or boron) covalently bonded to organic linking groups. Examples of PCPs include the series of structures known as iso-reticular MOFs (IRMOFs), composed of zinc ions coordinated to carboxylate anions, and the so-called MIL-series of iron-, chromium-, and aluminum carboxylates (MIL stands for "Materials of Institut Lavoisier," a research center associated with Versailles Saint-Quentin-en-Yvelines University, France). Other well-known examples of PCPs include, but are not limited to, CuBTC (also known as HKUST-1), which is short-hand nomenclature for copper (II) benzene-1,3,5-tricarboxylate [chemical formula $Cu_3(BTC)_2(H_2O)_3$], NOTT-100 (biphenyl-3,3',5,5'-tetracarboxylic acid), NOTT-101 (terphenyl-3,3',5,5'-tetracarboxylic acid), and ZIF-8 (Zn $(mim)_2.2H_2O$ where mim stands for methylimidazole).

PCP coatings on sensors possess a number of features that make them potentially superior to polymers and other coatings currently used to impart sensitivity and selectivity to chemical sensors. Firstly, PCP crystal structures and the chemical makeup of their pore structure can be tailored so that they have high selective affinity for a variety of analyte species. This contrasts with other nanoporous materials, such as zeolites, aerogels, synthetic opals, and nanotubes (both carbon- and non-carbon based). Secondly, PCPs have been observed to possess BET surface areas of up to 7000 $m^2/g$, a result approximately seven times greater than a zeolite. This makes these materials potentially highly effective sorbents that would increase sensitivity in sensors detecting either mass or stress changes. Third, the ability to tailor PCP pore sizes by changing the chemical nature of the linking molecule, changing the metal center, or changing the pore geometry, enables both the chemical selectivity and adsorption properties to be optimized in a rational way. Fourth, effective mechanical linkages between PCP crystalline or amorphous layers and a substrate can be created by covalent bonding schemes that anchor the PCP to the sensor surface. These qualities result in robust, stable sensors capable of generating large signals from small quantities of targeted analytes.

SUMMARY

The need for real-time, compact, and inexpensive chemical detectors is important for applications such as hazardous gas detection, personal exposure monitors, and humidity measurement. However, these applications pose many technical challenges because they require high sensitivity and specificity in small, economical packages with low power' consumption. New sensing concepts based on micro-electrical-mechanical systems (MEMS) offer a potential solution that can be mass-produced at low cost. Embodiments of the invention disclosed herein are directed to sensing devices based on a surface acoustic wave (SAW) device having an absorbent layer for detecting at least one chemical analyte in a gaseous carrier. Embodiments of methods for detecting the presence of a chemical analyte in a gaseous carrier using such devices are also disclosed.

In an embodiment, a sensing device for detecting at least one chemical analyte is disclosed. The sensing device includes a SAW sensor device having at least one surface, and a substantially continuous or substantially discontinuous absorbent layer bonded to the at least one surface of the SAW sensor device. The absorbent layer includes a PCP having a porous structure. The absorbent layer may be crystalline in nature with a substantially repeating lattice structure or the absorbent layer may be amorphous. Adsorption of at least one chemical analyte by the PCP causes mass changes in the PCP that dampens propagation of a standing acoustic wave through the SAW sensor device during propagation therethrough, thereby signaling a presence of the at least one chemical analyte.

In another embodiment, a SAW sensor device for detecting the presence of a chemical analyte in a gaseous carrier is disclosed. The SAW sensor device includes SAW device and a substantially continuous or substantially discontinuous absorbent layer bonded to at least one surface of the SAW device. The SAW device includes a substrate having one or more input interdigital transducers (IDTs) configured to convert an input electrical signal to a surface acoustic wave and one or more output IDTs configured to convert the surface acoustic wave to an output electrical signal. The adsorbent layer includes a MOF material having a porous structure. The MOF may be crystalline in nature with a substantially repeating lattice structure or the absorbent layer may be amorphous. Adsorption of at least one chemical analyte by the MOF material causes a mass change in the MOF material that alters propagation of a standing acoustic wave through the substrate layer during propagation therethrough, thereby signaling an amount of the at least one chemical analyte absorbed by the MOF material.

In yet another embodiment, a method for detecting a presence of a chemical analyte in a gaseous carrier is disclosed. The method includes (1) positioning a SAW device in contact with a gaseous carrier, (2) adsorbing at least one chemical analyte present in the gaseous carrier into the PCP, and (3) sensing adsorption of the at least one chemical analyte by the PCP, wherein adsorption of the at least one chemical analyte by the PCP causes mass changes in the PCP that dampens propagation of a standing acoustic wave through the substrate layer, thereby signaling the presence of the at least one chemical analyte.

The sensing devices and methods for their use may be configured for sensing chemical analytes selected from water vapor, carbon dioxide, methanol, ethanol, carbon monoxide, nitric oxide, nitrous oxide, organic amines, organic compounds containing $NO_2$ groups, halogenated hydrocarbons (e.g., trihalomethanes, such as chloroform), acetone, hexane, toluene, isopropanol, alcohols, alkanes, alkenes, benzene, functionalized aromatics (e.g., compounds based on benzene but with one or more chemical groups added), ammonia ($NH_3$), phosgene ($COCl_2$), sulfur mustard, nerve agents (e.g., Sarin and VX), sulfur dioxide, tetrahydrofuran (THF) and methyltertbutyl ether (MTBE) and combinations thereof.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify the above and other advantages and features of embodiments of the invention, a more particular description will be rendered by reference to specific embodiments thereof which are illustrated in the appended drawings. It is appreciated that these drawings depict only illustrated embodiments of the invention and are therefore not to be considered limiting of its scope. The embodiments of the invention will be described and explained with additional specificity and detail through the use of the accompanying drawings in which.

DETAILED DESCRIPTION

I. Introduction

The need for real-time, compact, and inexpensive chemical detectors is important for applications such as hazardous gas detection, personal exposure monitors, and humidity measurement. However, these applications pose many technical challenges because they require high sensitivity and specificity in small, economical packages with low power consumption. New sensing concepts based on MEMS offer a potential solution that can be mass-produced at low cost. Embodiments of the invention disclosed herein are directed to sensing devices based on a SAW device coated with an absorbent layer for detecting at least one chemical analyte in a gaseous carrier. Embodiments of methods for detecting the presence of a chemical analyte in a gaseous carrier using such devices are also disclosed.

When an absorbent layer adsorbs an analyte, it produces a mass change in the absorbent layer. This mass change can be used to determine the concentration of an analyte of interest (e.g., water vapor or chloroform) in a gaseous atmosphere. Various embodiments of the invention include a SAW device having an absorbent layer fixedly attached to one or more surfaces of the SAW device. A SAW device may include a substrate having at least two sets of IDTs formed thereon. An input IDT converts an electrical signal to a surface acoustic wave that propagates in the substrate and an output IDT converts the surface acoustic wave back into an electrical signal. The propagation of the surface acoustic wave and, as a result, the output electrical signal, are sensitive to mass changes in and around the substrate. As such, as the absorbent layer absorbs an analyte of interest, it causes a change in the propagation of the surface acoustic wave. The magnitude of the change (e.g., a phase shift in the surface acoustic wave) can be correlated to the amount of the analyte of interest adsorbed by the absorbent layer.

Suitable examples of absorbent layers include so-called PCP layers. MOF materials are a recently developed class of nanoporous, supramolecular PCP materials with tunable properties that make them very attractive for chemical sensing. MOFs are typically crystalline (but can sometimes be amorphous) coordination polymers in which metal cations are connected by organic, electrondonating "linker" groups. These serve as rigid struts, allowing the material to maintain its porosity when guest solvent molecules are removed. Very high surface areas can be achieved; Langmuir values as high as 6,000-10,000 $m^2/g$ have been reported. This is a value approximately six times greater than a zeolite. This makes these materials potentially highly effective sorbents that would increase sensitivity in sensors detecting either mass or stress changes.

Moreover, the presence of an organic component within the structure creates many opportunities to synthetically modify the pore environment with respect to both size and chemical properties. Previous experiments and modeling demonstrate that selective gas uptake and separation are achievable, although most of these results were obtained under high-pressure conditions that bear little resemblance to the conditions typically encountered by chemical sensors. Recent atomistic modeling we performed suggests that selective detection of a wide range of molecular species should be feasible.

A number of MOFs exhibit the ability to adsorb various classes of molecules including volatile organic compounds, polyaromatic hydrocarbons, explosives, nerve agents, and methane. An additional advantage of MOFs for sensing purposes is that they are very stable thermally. Most MOFs display decomposition temperatures in the range of 350-400° C., with a few decomposing above 500° C. (e.g., the UiO MOFs). These features, combined with their highly uniform pore structure, make them superior in many ways to other high-surface-area nanoporous materials, such as anodized aluminum oxide (AAO), porous carbons, and aerogels, as well as organic polymers used to provide sensor selectivity. Proof-of-concept experiments demonstrate that chemical detection based on several MOF-enabled transduction mechanisms is feasible. For example, sensors based on impedance, colorimetry, interferometry, plasmonics, and luminescence have been described. In addition, U.S. Pat. No.

8,065,904, the entirety of which is incorporated herein by reference, describes sensing devices and methods based on PCP-coated strain detectors (i.e., microcantilevers). In most cases, however, the bench-scale experiments performed on a specific material do not involve full integration of the MOF into a self-contained sensing device. Responses to analytes are demonstrated, but detection limits are left undetermined.

Depending upon the application, PCP layers are chosen for their compatibility with their environment. For instance, if a SAW sensor constructed with a shear-horizontal mode was to be used to detect trace material in a liquid media, the PCP layer is selected from materials which are stable in the media, or if the sensor is deployed in a gaseous atmosphere, the PCP layer is selected from materials that do not react irreversibly with the gas or gases of the target atmosphere. For example, zinc-carboxylate metal organic frameworks (MOFs) such as IRMOF-1 may be appropriate for detection of gases in dry atmospheres, while the nickel MOF $Ni_2(4,4'\text{-bipyridine})_3(NO_3)_4$ could be used for detecting analytes in organic solvents. Alternatively, a humidity-stable MOF such as CuBTC (also known as HKUST-1), which is short-hand nomenclature for copper (II) benzene-1,3,5-tricarboxylate [chemical formula $Cu_3(BTC)_2(H_2O)_3$] (where BTC is benzene-1,3,5-tricarboxylate) could be employed for detection in humid media. MOFs such as various ZIF compounds (e.g. ZIF-8) or zirconium-based UiO MOFs (e.g., UiO-66), which are stable in liquid water, could be used to detect species in aqueous solution. ZIFs are also highly useful for size-selective detection, due to their rather small pore openings (typically 2-5 Å). MOFs with open coordination sites, such as CuBTC and MOF-74 and its extended versions are attractive for detecting weakly interacting gases, such as $CO_2$ and $CH_4$, and molecules such as $O_2$ and NO.

Embodiments of the invention described herein are directed to SAW-based sensors that may be used to detect and quantify a variety of analytes, such as, but not limited to, water vapor, carbon dioxide, methanol, ethanol, carbon monoxide, nitric oxide, nitrous oxide, organic amines, organic compounds containing $NO_2$ groups, halogenated hydrocarbons (e.g., trihalomethanes, such as chloroform), acetone, hexane, toluene, isopropanol, alcohols, alkanes, alkenes, benzene, functionalized aromatics (e.g., compounds based on benzene but with one or more chemical groups added), ammonia ($NH_3$), phosgene ($COCl_2$), sulfur mustard, nerve agents (e.g., Sarin and VX), sulfur dioxide, tetrahydrofuran (THF) and methyltertbutyl ether (MTBE) and combinations thereof. For example, herein it is shown that a thin film of Cu-BTC grown on a SAW sensor may be used to detect water vapor at sub-parts per million by volume ("ppmv") concentrations, demonstrating that functionalizing devices with MOF materials may enable highly sensitive gas detection. The MOF-coated SAWs sensors described herein exhibit a rapid and reversible response to water vapor concentrations, spanning 4 orders of magnitude from −85° C. to +10° C. frost point (0.28-14,800 ppm at 632 mmHg atmosphere pressure. The response time is comparable to precision sensors. Though precision and accuracy are reduced compared to these methods, the devices described herein are quite simple and robust. No cross-sensitivity to $N_2$, $O_2$, $CO_2$, Ar, or methane was observed.

The MOF layer in the SAW-based sensors described herein may be covalently bound to surface hydroxyl groups of the SAW substrate (e.g., a quartz surface). This provides a much stronger mechanical coupling than is possible with the self-assembled monolayers (SAM) of typical devices. In addition to describing the sensor performance, the relationship between film thickness and device response is demonstrated.

Because of their low cost, robustness, and the relative ease of coating (compared with MEMS devices such as microcantilevers), SAWs are a convenient platform for evaluating MOF coatings for gas sensing and are suited for practical use as well. These qualities result in robust, stable sensors capable of generating large signals from small quantities of targeted analytes.

II. Saw-Based Sensing Devices

Figure 1A:
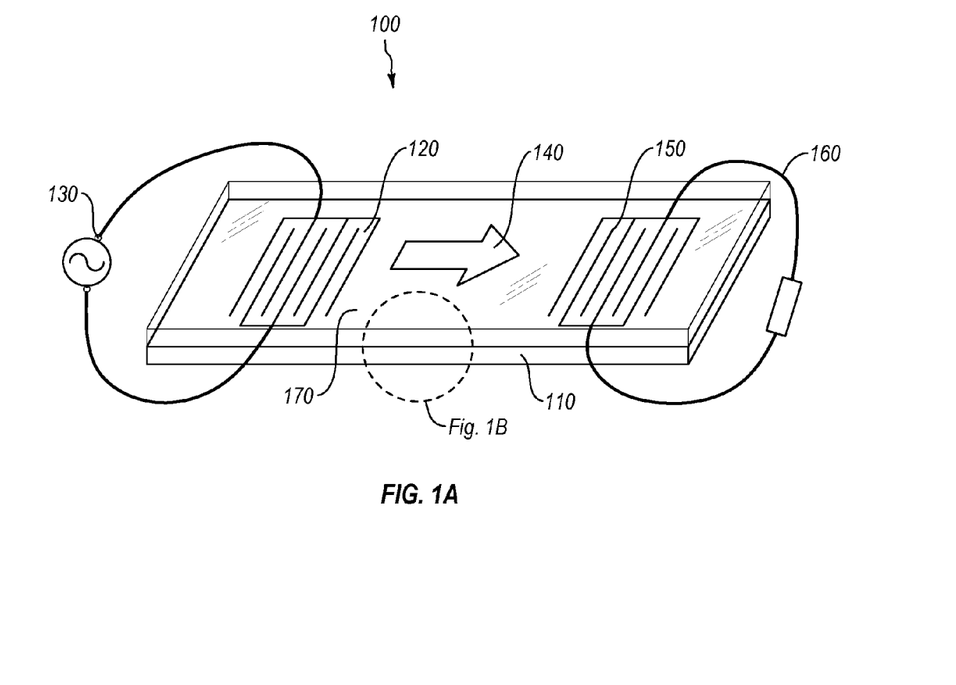
FIG. 1A schematically illustrates a SAW sensor according to an embodiment of the invention.

Referring now to FIG. 1A, a typical SAW-based sensor 100 is schematically illustrated. The SAW-based sensor 100 is based on a SAW device that includes a piezoelectric substrate layer 110, an input interdigitated transducer 120, an input electrical circuit 130, an output interdigitated transducer 150, and an output electrical circuit 160. The SAW device illustrated in FIG. 1A is a relatively simple SAW device. Other SAW devices may include additional transducers and/or additional circuits.

When the input interdigitated transducer 120 is stimulated by the input electrical circuit 130, the input interdigitated transducer 120 converts electrical charge to mechanical deformation of the substrate 110 surface at an oscillating frequency related to the alternating frequency of an input electrical signal. The input electrical signal generates a surface acoustic wave through the inverse piezoelectric effect that propagates through the substrate 110, which is illustrated schematically by arrow 140. When the surface acoustic wave 140 impacts the output interdigitated transducer 150, the surface acoustic wave 140 is converted back into an electrical signal by the direct piezoelectric effect which generates an output electrical signal at the interdigitated transducer 150. The magnitude of the output electrical signal is directly related to the magnitude of the surface acoustic wave 140.

The device 100 illustrated in FIG. 1A further includes a PCP layer 170 that is attached to the substrate layer 110. The PCP layer 170 may, for example, be directly attached (e.g., covalently attached) to the substrate layer 110 or it may be attached to the substrate layer 110 though an intermediate layer such as a self-assembled monolayer (SAM).

As discussed above, the PCP layer 170 has a porous structure and is capable of selectively interacting with a wide variety of chemical entities. When molecules are adsorbed or absorbed by the PCP layer 170, the mass density of the PCP layer 170 increases. This increase in mass density alters or retards propagation of the surface acoustic wave 140 through the device 100, which may be registered, for example, as a phase shift in the surface acoustic wave 140 that is directly proportional to the amount of material adsorbed by the PCP layer.

Figure 1B:
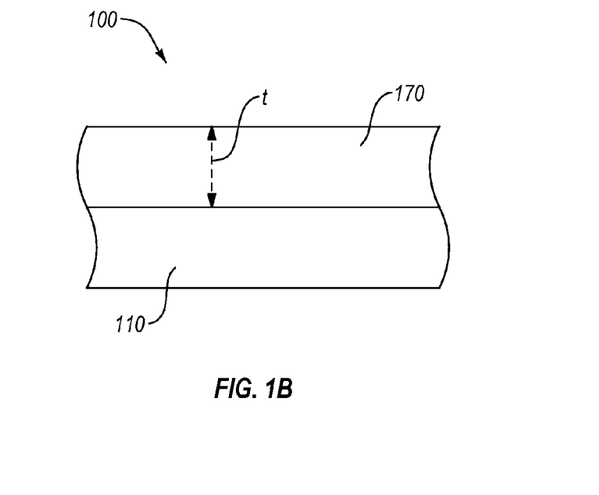
FIG. 1B illustrates a side elevation view of the SAW sensor of FIG. 1A according to an embodiment of the invention.

Referring now to FIG. 1B, a side elevation view of the sensor device 100 of FIG. 1A is illustrated. As discussed above, the device 100 includes the substrate 110 and the PCP layer 170. Suitable examples of materials that may be used for SAW substrates include, but are not limited to, piezoelectric materials such as single crystal quartz, lithium niobate, aluminum nitride, and zinc oxide. The PCP layer 170 may be fabricated from any one of the materials discussed herein or from any suitable PCP material known in the art.

The PCP layer 170 has a thickness t. Generally, the thickness t will exist in a range depending on the sensing application and the type of PCP used. For example, some PCPs and some analytes respond better to thicker coatings. How thick is useful depends on the properties of a particular PCP and how it interacts with its analyte. For instance, rapid response time may not be important in some applications where long, slow changes may take place. In such a case, a thicker coating may be appropriate. In cases where the sensor device needs to respond to rapid changes in the PCP, a thinner coating may be appropriate.

In one embodiment, the PCP layer may have a thickness in a lower range from about 30 nm, 50 nm, 100 nm, 125 nm, 150 nm, 175 nm, 200 nm, 250 nm or 300 nm, a thickness in an upper range from about 300 nm, 350 nm, 400 nm, 450 nm, 500 nm, 600 nm, 700 nm, 800 nm, 900 nm, 1000 nm, 1250 nm, 1500 nm, 1750 nm, 2000 nm, or any combination of the above recited lower and upper ranges.

For humidity sensing with a Cu-BTC-based SAW sensor, for example, it was found that thinner coatings (e.g., about 30 nm) have low sensitivity and poor response. However, coating thickness cannot be increased to an arbitrarily large value without impacting performance. The response to water vapor reaches a maximum value at a thickness of about 200 nm. Thicker coatings add mass at a distance from the surface that does not couple well with the surface acoustic waves but continues to dampen the energy nonetheless. In addition, coatings of about 200 nm and thicker showed progressively longer equilibration times, with a ~350 nm coated SAW failing to level off after 4-6 h of constant exposure. In contrast, the experimentally determined preferred thickness for a ZIF-8-based SAW sensor for sensing acetone is about 500 nm.

The PCP layer 170 may be deposited by a number of methods known in the art. For example, Cu-BTC layers may be deposited on SAW substrate layers 110 by a layer-by-layer ("LBL") growth method. In a typical procedure, SAW-bearing substrates 110 were sequentially dipped in alternating ethanolic solutions of 1.0 mM copper acetate (Cu(OAc)2) and 0.1 mM trimesic acid (1,3,5-benzenetricarboxylic acid, H3BTC) for 5-20 min each (e.g., 5 min in the copper acetate solution and 10 min in the trimesic acid solution) at 50° C. in a static reaction vessel. Two 10 min ethanol rinses followed each growth step to remove excess reagent from the surface. In the process, the initial layer covalently attaches to the substrate (e.g., a quartz substrate), and each subsequent cycle grows the Cu-BTC thickness by a controlled increment. In order to increase the number of covalent interactions between the substrate and the Cu-BTC, the substrate may be treated with oxygen plasma to increase the density of hydroxyl groups on the surface of the substrate prior to coating with Cu-BTC. A ligand exchange reaction takes place whereby newly introduced solvated metal ions coordinate to ligands already bound to the previous MOF layer. Exposure time, temperature, and solution concentration may be controlled to establish a constant growth rate. SAW devices may be coated by manually dipping the substrate in the alternating solution or automated procedures may be employed.

Figure 2:
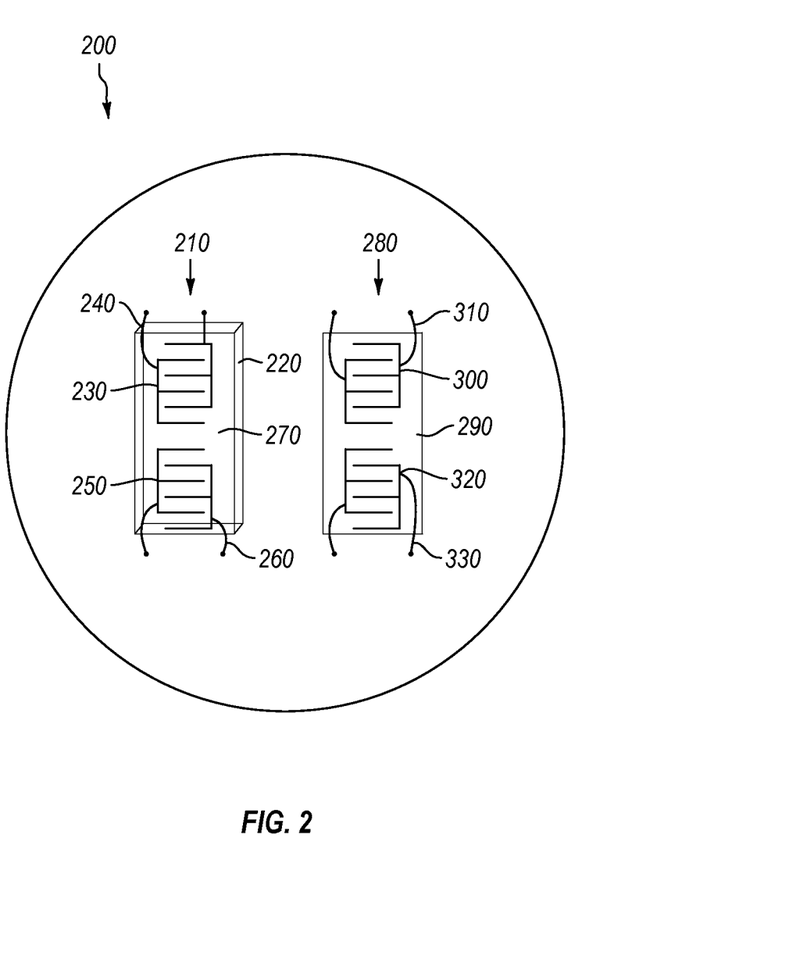
FIG. 2 illustrates a sensor device having a sensor SAW device and a reference SAW device according to an embodiment of the invention.

Referring now to FIG. 2, a sensor device 200 that includes a sensor SAW device 210 and a reference SAW device 280 is illustrated. The sensor SAW device 210 is essentially the same or similar to the device 100 illustrated in FIG. 1A. The sensor SAW device 210 includes a substrate layer 220, an input interdigitated transducer 230, an input electrical circuit 240, an output interdigitated transducer 250, and an output electrical circuit 260. The sensor SAW device 210 further includes a PCP layer 270 fabricated from a microporous material (e.g., Cu-BTC) that is selected for interacting with an analyte of interest. The reference SAW device 280 includes a substrate layer 290, an input interdigitated transducer 300, an input electrical circuit 310, an output interdigitated transducer 320, and an output electrical circuit 330. The reference SAW device 280 either does not include a PCP layer, or the reference SAW device 280 may have a PCP layer 270 if the reference SAW remains isolated from the chemicals to be sensed.

The sensor device 200 may further include components such as a sealed, chemically inert housing, one or more heaters for "baking out" the SAW sensors 210 and 280, and one or more fittings for delivering a gas stream to the sensor 200. In an embodiment, the sensor device 200 may be configured as a flow cell. In sensing applications, a gas stream with vapors may be passed over both SAW sensors 210 and 280. The reference SAW device 280 provides a constant reference for baselining the response of the sensor SAW device 210 to adsorption of a chemical analyte.

III. Saw-Based Sensing Methods

In an embodiment, a method for detecting the presence of a chemical analyte in a gaseous carrier is disclosed. The method includes (1) positioning a SAW sensor device in contact with a gaseous carrier, (2) adsorbing at least one chemical analyte present in the gaseous carrier into the PCP, and (3) sensing adsorption of the at least one chemical analyte by the PCP, wherein adsorption of the at least one chemical analyte by the PCP causes mass changes in the PCP that dampens propagation of a standing acoustic wave through the substrate layer, thereby signaling the presence of the at least one chemical analyte. The SAW sensor device and methods for its fabrication are described in greater detail elsewhere herein.

In an embodiment, the sensing includes quantifying the amount of the at least one chemical analyte adsorbed by the PCP. The amount of the at least one chemical analyte adsorbed by the PCP may be quantified in terms of a phase shift in the surface acoustic wave as the PCP interacts with the analyte. In an embodiment, the sensing includes sensing molecular species selected from the group consisting of water vapor, carbon dioxide, methanol, ethanol, carbon monoxide, nitric oxide, nitrous oxide, organic amines, organic compounds containing NO2 groups, halogenated hydrocarbons (e.g., trihalomethanes, such as chloroform), acetone, hexane, toluene, isopropanol, alcohols, alkanes, alkenes, benzene, functionalized aromatics (e.g., compounds based on benzene but with one or more chemical groups added), ammonia (NH3), phosgene (COCl2), sulfur mustard, nerve agents (e.g., Sarin and VX), sulfur dioxide, tetrahydrofuran (THF) and methyltertbutyl ether (MTBE) and combinations thereof in the gaseous carrier. In an embodiment, the method further comprises positioning a reference SAW device in contact with the gaseous carrier, wherein the reference SAW device provides a baseline reference, and wherein the reference SAW device includes a SAW structure without an absorbent layer bonded thereto.

IV. Examples

Example 1

Figure 3:
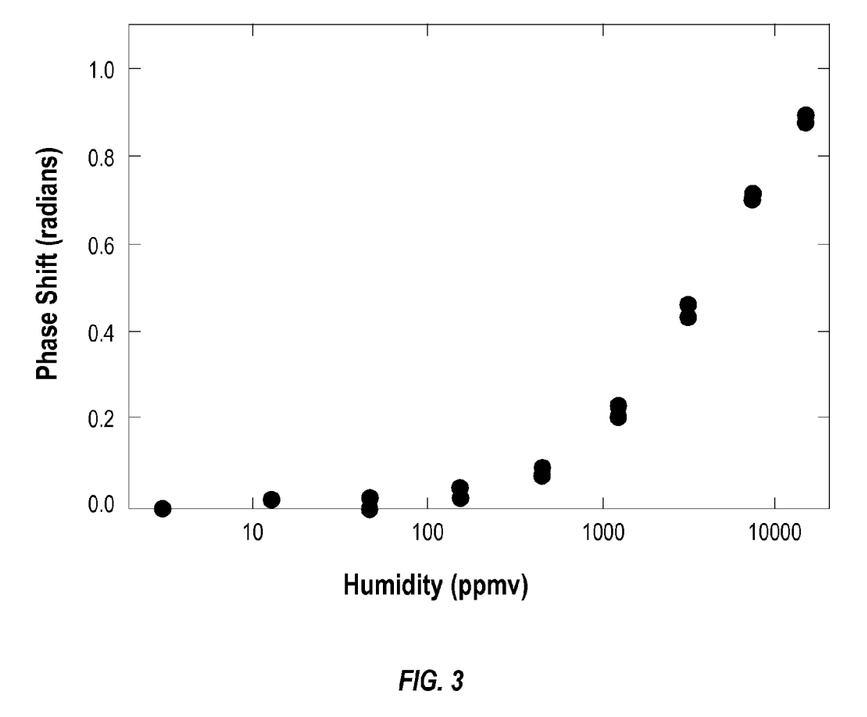
FIG. 3 is a graph illustrating the response of a Cu-BTC SAW device to different humidity levels according to an embodiment of the invention.

Referring now to FIG. 3, the use of a SAW device coated with a MOF thin film to detect water vapor across a wide concentration range is demonstrated. A range of about 3-14,800 ppmv (reference atmospheric pressure of 632 mmHg) was delivered to sensor SAWs coated with thin films of Cu-BTC deposited by an automated layer-by-layer method. Devices coated by a manual technique demonstrated sensitivity from about 0.28-14,800 ppmv. This exceeds the sensitivity and range of many commercially available sensors. Cu-BTC layers were covalently bonded directly to the silicon oxide surface of a quartz SAW, allowing devices to be heated beyond 100° C. to desorb water adsorbed in the pores without decomposition, thereby regenerating the sensors. Additional data illustrate that these sensors are capable of a rapid and reproducible response to water vapor concentration. These results provide convincing evidence that MOF functionalization of compact sensing technologies such as SAW devices can compete with state of the art devices.

Example 2

Figure 4:
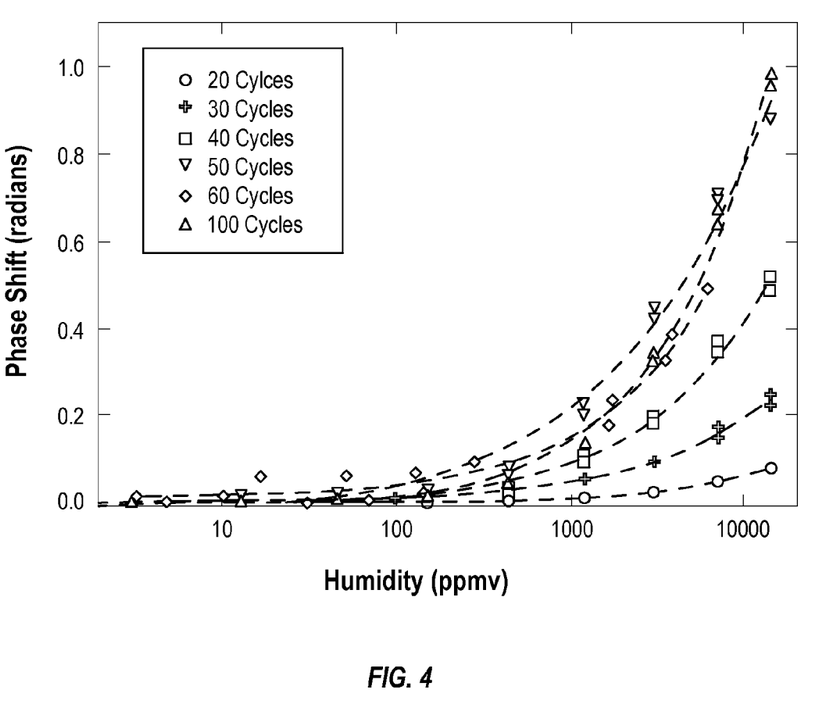
FIG. 4 is a graph illustrating the response of Cu-BTC SAWs for coatings of different thicknesses (i.e., different numbers of coating cycles) to various humidity levels.

Referring now to FIG. 4, the response to humidity of SAWs with different coating thicknesses (i.e., different numbers of layer-by-layer ("LBL") coating cycles) is shown. FIG. 4 shows testing for coatings of 20-100 cycles (from 70 to 350 nm thick). As can be seen in FIG. 4, the response to humidity appears linear at low concentrations on this log-linear plot as the MOF layer accumulates water. Subsequently, higher accumulation levels of water produce a steeper slope. Other experimental and modeling data suggest that the response will have another inflection above 50% relative humidity (>12° C. frost point) and asymptotically approach a final value as water saturates the pores of the MOF layer.

FIG. 4 also illustrated that thinner coatings have lower sensitivity, with a very poor response for 10 cycle-coated (not shown) and 20 cycle-coated SAWs. However, coating thickness cannot be increased to an arbitrarily large value without impacting performance. As seen in FIG. 4, the response to water vapor reaches a maximum value at 60 coating cycles, which equates to an approximate thickness of 200 nm. Thicker coatings add mass at a distance from the surface that does not couple well with the surface acoustic waves but continues to dampen the energy nonetheless. In addition, 60 and 100 cycle SAWs showed progressively longer equilibration times, with the 100 cycle SAWs failing to level off after 4-6 h of constant exposure.

The automated LBL process produces uniform and reproducible Cu-BTC coatings but is relatively slow. This process requires approximately 20 h to deposit a 100-nm film at room temperature, although it was recently determined that film growth at 62° C. can reduce this by a factor of about 2.60. A manual procedure can also be used, in which devices are alternately submerged in solutions of copper acetate and trimesic acid. Growth by this method is faster, yielding 150-nm thick coatings in only 6 h. Aside from the tedious nature of the process, it was found that coating uniformity with this method is more difficult to control than with the automated LBL process. However, the sensitivity of these devices is higher than devices coated by the automated method. Sensors coated with the automated method have a demonstrated range of about 3-14,800 ppmv and sensors coated with the manual method demonstrated sensitivity from about 0.28-14,800 ppmv. It is currently believed by the inventors that the greater sensitivity range of the manually coated sensors results from greater non-uniformity in the surface coating as compared to sensors prepared via the automated method.

Example 3

Figure 5:
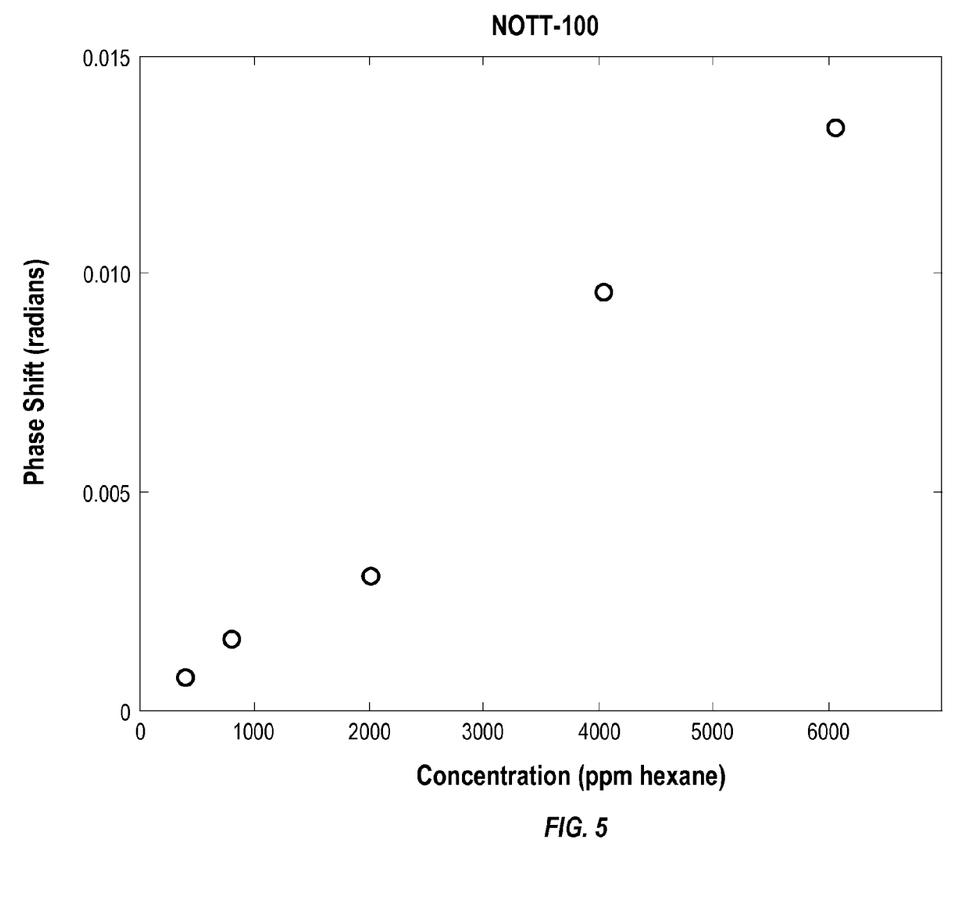
FIG. 5 is a graph illustrating the response of a NOTT-100 coated SAW device to different hexane concentration levels according to an embodiment of the invention.
Figure 6:
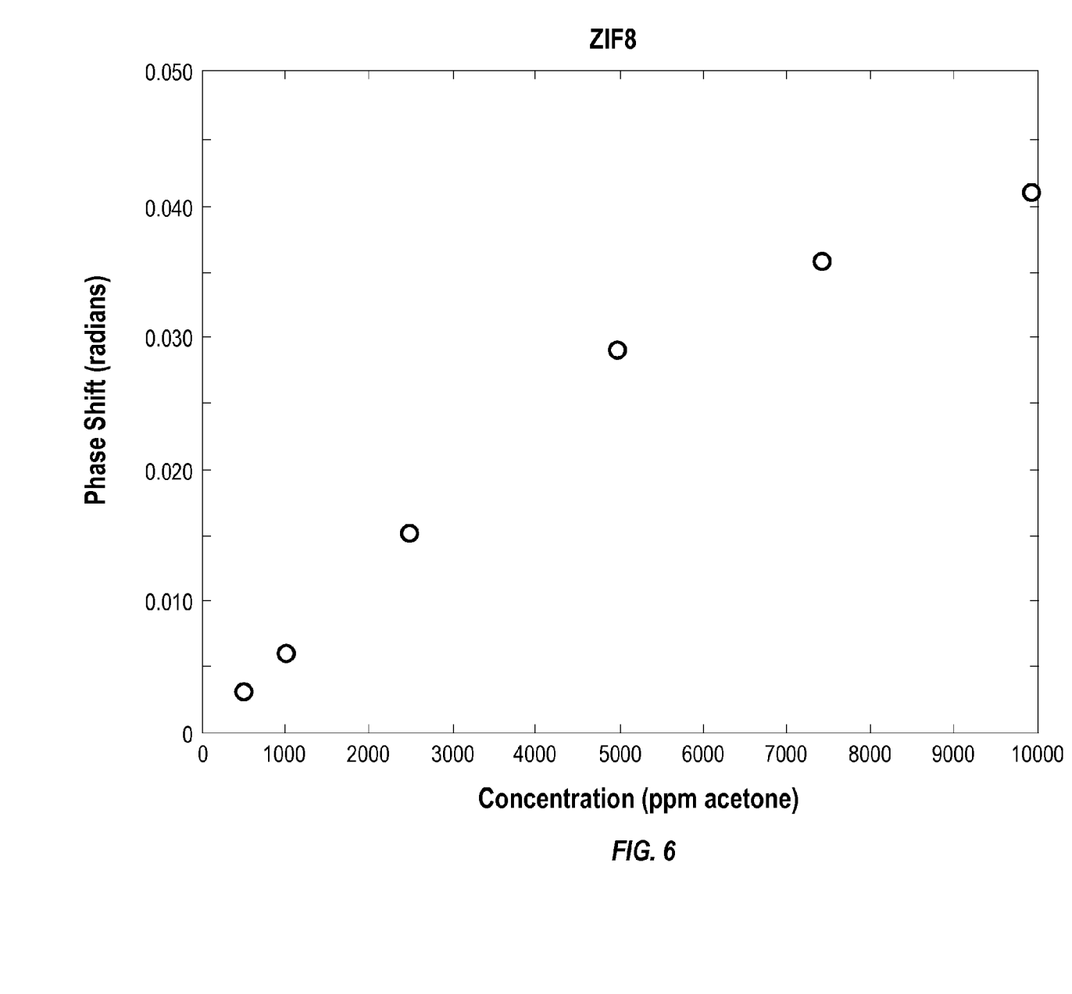
FIG. 6 is a graph illustrating the response of a ZIF-8 coated SAW device to different hexane concentration levels according to an embodiment of the invention.

Referring now to FIGS. 5 and 6, detection of hexane and acetone with SAW devices coated with NOTT-100 and ZIF8 is illustrated. FIG. 5 illustrated that a NOTT-100 coated SAW device detected a broad range of hexane concentrations (e.g., about 400 ppm to about 6070 ppm). Adsorption of hexane by NOTT-100 was reversible and the detection effect was reproducible. Similarly, FIG. 6 illustrated that a SAW device coated with ZIF8 detected a broad range of acetone concentrations (e.g., about 495 ppm to about 9910 ppm). Response was reversible with the response returning to baseline after the removal of acetone.

In addition to the foregoing, data presented in U.S. Provisional Application No. 61/544,078, the entirety of which is incorporated herein by reference, illustrates that a practical Cu-BTC-based sensor capable of detecting chloroform vapor is feasible. And while the specific sensor discussed in U.S. Prov. App. Ser. No. 61/544,078 is based on microcantilever detection, the inventors currently believe that such a sensor may also be based on a SAW device. In addition, the results presented herein and in U.S. Provisional Application No. 61/544,078 illustrate that PCP materials (e.g., MOFs) may interact selectively with wide ranging chemical species and that, as a result, SAW-based sensors using such PCP materials may be fabricated and used for sensing and quantifying wide ranging chemical species.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sensing device for detecting at least one chemical analyte, comprising:
    a surface acoustic wave ("SAW") sensor device having at least one surface; and
    an absorbent layer bonded to the at least one surface of the SAW sensor device, wherein the absorbent layer comprises a porous coordination polymer ("PCP") having a porous structure, wherein adsorption of at least one chemical analyte by the PCP causes mass changes in the PCP that dampens propagation of a standing acoustic wave through the SAW sensor device during propagation therethrough, thereby signaling a presence of the at least one chemical analyte;
    wherein the PCP is covalently bonded to the SAW sensor device.

2. The sensing device of claim 1, wherein the PCP comprises a metal organic framework ("MOF").

3. The sensing device of claim 1, wherein a degree of dampening of propagation of the standing acoustic wave through the SAW sensor device is proportional to an amount the at least one analyte adsorbed by the PCP.

4. The sensing device of claim 1, wherein the PCP is grown from one or more reactant solutions onto the SAW sensor device.

5. The sensing device of claim 4, wherein the PCP is grown onto the SAW sensor device by a layer-by-layer method.

6. The sensing device of claim 4, wherein the reactant solutions comprise benzene-1,3,5-tricarboxylic acid and copper acetate dissolved in a quantity of ethanol.

7. A surface acoustic wave sensor device for detecting the presence of a chemical analyte in a gaseous carrier, comprising:
    a substrate layer having use one or more input interdigital transducers ("IDTs") configured to convert an input electrical signal to a surface acoustic wave in the substrate layer and one or more output IDTs configured to convert the surface acoustic wave to an output electrical signal; and
    a substantially continuous or substantially discontinuous absorbent layer bonded to at least one surface of the substrate layer, wherein the absorbent layer comprises a metal-organic framework ("MOF") material having a porous structure, wherein adsorption of at least one chemical analyte by the MOF material causes a mass change in the MOF material that alters propagation of a standing acoustic wave through the substrate layer during propagation therethrough, thereby signaling an amount of the at least one chemical analyte adsorbed by the MOF material;

wherein the absorbent layer is covalently bonded to the substrate layer.

8. The sensor device of claim 7, wherein the MOF material comprises copper (II) benzene-1,3,5-tricarboxylate (CuBTC).

9. The sensor device of claim 7, wherein the sensor device senses molecular species selected from the group consisting of water vapor, carbon dioxide, methanol, ethanol, carbon monoxide, nitric oxide, nitrous oxide, organic amines, organic compounds containing $NO_2$ groups, halogenated hydrocarbons, acetone, hexane, toluene, isopropanol, alcohols, alkanes, alkenes, benzene, functionalized aromatics, ammonia ($NH_3$), phosgene ($COCl_2$), sulfur mustard, nerve agents, sulfur dioxide, tetrahydrofuran (THF) and methyltertbutyl ether (MTBE) and combinations thereof.

10. A method for detecting a presence of a chemical analyte in a gaseous carrier, the method comprising:

positioning a surface acoustic wave ("SAW") device in contact with a gaseous carrier, wherein the SAW sensor device includes:

a substrate layer having use one or more input interdigital transducers ("IDTs") configured to convert an input electrical signal to a surface acoustic wave in the substrate layer and one or more output IDTs configured to convert the surface acoustic wave to an output electrical signal; and a substantially continuous or a substantially discontinuous absorbent layer bonded to at least one surface of the substrate layer, wherein the absorbent layer comprises a porous coordination polymer ("PCP") having a porous structure;

adsorbing at least one chemical analyte present in the gaseous carrier into the PCP; and sensing adsorption of the at least one chemical analyte by the PCP, wherein adsorption of the at least one chemical analyte by the PCP causes mass changes in the PCP that dampens propagation of a standing acoustic wave through the substrate layer, thereby signaling the presence of the at least one chemical analyte wherein the PCP is covalently bonded to the SAW sensor device.

11. The method of claim 10, wherein the PCP comprises a metal organic framework.

12. The method of claim 10, wherein the PCP comprises one of a covalent organic frameworks (COF) or a zeolitic imidazolate framework (ZIF).

13. The method of claim 10, positioning a reference SAW device in contact with the gaseous carrier, wherein the reference SAW device provides a baseline reference, and wherein the reference SAW device includes a SAW structure without an absorbent layer bonded thereto.

14. The method of claim 10, wherein the sensing includes sensing molecular species selected from the group consisting of water vapor, carbon dioxide, methanol, ethanol, carbon monoxide, nitric oxide, nitrous oxide, organic amines, organic compounds containing $NO_2$ groups, halogenated hydrocarbons, acetone, hexane, toluene, isopropanol, alcohols, alkanes, alkenes, benzene, functionalized aromatics, ammonia ($NH_3$), phosgene ($COCl_2$), sulfur mustard, nerve agents, sulfur dioxide, tetrahydrofuran (THF) and methyltertbutyl ether (MTBE) and combinations thereof in the gaseous carrier.

15. The sensing device of claim 1, wherein the PCP is a hybrid inorganic-organic crystalline material with a pore structure and chemical properties that can be tailored by a selection of component chemical moieties and self-organize into two- and three-dimensional open-pore structures.

16. The sensor device of claim 7, further comprising a reference SAW device for providing a baseline reference, wherein the reference SAW device includes a SAW structure without an absorbent layer bonded thereto.

17. The sensor device of claim 7, wherein the MOF is grown from one or more reactant solutions onto the SAW sensor device, wherein the reactant solutions comprise benzene-2-R',4-R",6-R'''-1,3,5-tricarboxylic acid and R', R", and R''' are H, X (where X is halogen), alkyl, OH, $NO_2$, $NH_2$, OR (where R is an alkyl group) or any other chemical atom or group attached at these positions, and copper acetate dissolved in a quantity of ethanol.

18. The sensor device of claim 7, wherein the sensor device senses molecular species selected from the group consisting of water vapor, carbon dioxide, methanol, ethanol, carbon monoxide, halogenated hydrocarbons, acetone, hexane, toluene, isopropanol, alcohols, alkanes, alkenes, benzene, functionalized aromatics, phosgene ($COCl_2$), sulfur mustard, nerve agents, sulfur dioxide, tetrahydrofuran (THF) and methyltertbutyl ether (MTBE), and combinations thereof.

19. The sensor device of claim 7, wherein the substrate layer is treated with oxygen plasma prior to the absorbent layer covalently bonding to the substrate layer.

20. The sensor device of claim 17, wherein the SAW sensor device is treated with oxygen plasma prior to coating with the one or more reactant solutions.

* * * * *